United States Patent
Mochly-Rosen

(10) Patent No.: US 7,507,711 B2
(45) Date of Patent: *Mar. 24, 2009

(54) PEPTIDE INHIBITORS OF PROTEIN KINASE C

(75) Inventor: Daria Mochly-Rosen, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 96 days.

This patent is subject to a terminal disclaimer.

(21) Appl. No.: 10/421,503

(22) Filed: Apr. 22, 2003

(65) Prior Publication Data

US 2004/0009922 A1    Jan. 15, 2004

Related U.S. Application Data

(60) Provisional application No. 60/374,530, filed on Apr. 22, 2002.

(51) Int. Cl.
*A61K 38/00* (2006.01)

(52) U.S. Cl. .................................. 514/12; 530/300

(58) Field of Classification Search ................ None
See application file for complete search history.

(56) References Cited

U.S. PATENT DOCUMENTS

| | | | |
|---|---|---|---|
| 4,351,829 | A | 9/1982 | Zetler et al. |
| 5,776,685 | A | 7/1998 | Riedel |
| 5,783,405 | A | 7/1998 | Mochly-Rosen et al. |
| 5,935,803 | A | 8/1999 | Vasquez et al. |
| 6,165,977 | A | 12/2000 | Mochly-Rosen |
| 6,376,467 | B1 | 4/2002 | Messing et al. |
| 6,395,306 | B1 * | 5/2002 | Cui et al. ............. 424/539 |
| 2003/0223981 | A1 | 12/2003 | Mochly-Rosen et al. |
| 2005/0215483 | A1 | 9/2005 | Mochly-Rosen |

FOREIGN PATENT DOCUMENTS

| | | | |
|---|---|---|---|
| WO | WO 94/04686 | * | 3/1994 |
| WO | WO 97/14038 A1 | | 4/1997 |
| WO | WO 99/43805 | * | 9/1999 |
| WO | WO 00/01415 | | 1/2000 |
| WO | WO 00/53218 A1 | | 9/2000 |
| WO | WO 01/46252 | * | 6/2001 |
| WO | WO 01/75067 A2 | | 10/2001 |

OTHER PUBLICATIONS

Ono, Y. et al. Science 236: 1116-1120 (1987).*
Kubo, K. et al. FEBS Lett. 223(1): 138-142 (1987).*
Falnes et al., Biochemistry 40: 4349-4358 (2001), "Ability of the Tat basic domain and VP22 to mediate cell binding, but not membrane translocation of the Diptheria toxin A-fragment".*
Jones et al., Cell Regulation 2: 1001-1009 (1991), "Molecular cloning of a second form of rac protein kinase".*
Meier et al., Journal of Biological Chemistry 272(48): 30491-30497 (1997), "Mitogenic activation, phosphorylation, and nuclear translocation of protein kinase Bbeta".*
Gökmen-Polar et al., "Mapping of a molecular determinant for Protein Kinase C betaII isozyme function", Journal of Biological Chemistry 273(32): 20261-20266 (1998).*
Chen, L., et al., *PNAS 98*(20):11114-11119, (2001).
Julius, D. and Basbaum, A.I., *Nature, 413*:203-210, (2001).
Igwe, O.J. and Chronwall, B.M., *Neuroscience 104*(3):875-890, (2001).
Martin, W.J., et al., *Neuroscience 88*(4):1267-1274, (1999).
Martin, W.J., et al., *The Journal of Neuroscience 21*(14):5321-5327, (2001).
Petersen-Zeitz, K.R. and Basbaum, A.I., *Pain Supplement 6*:S5-S12, (1999).
Stebbins, E.G. and Mochly-Rosen, D., *J of Biological Chemistry 276*(32):29644-29650, (2001).
Wen, Z.H., et al., *Neuroscience Letters 309*:25-28, (2001).
Aley et al., *The Journal of Neurosceince, 20*(12):4680-4685 (2000).
Csukai et al., *Pharmacological Research, 39*(4):253-259 (1999).
Dina et al., *The Journal of Neurosceince, 20*(22):8614-8619 (2000).
Knopf et al., *Cell, 46*:491-502 (1986).
Malmberg et al., *Science, 278*:279-283 (1997).
Mochly-Rosen et al., *FASEB Journal, 12*:35-42 (1998).
Chen, L. et al., *Chemistry & Biology*, 8:1123-1129 (2001).
Sweitzer et al., "Developmental Regulation of Inflammatory Pain by Protein Kinase C", Society for Neuroscience Abstract Viewer and Itinerary Planner, 32nd Annual Meeting of the Society of Neuroscience (2002).

* cited by examiner

*Primary Examiner*—Anand U Desai
(74) *Attorney, Agent, or Firm*—Judy M. Mohr; Susan L. Harlocker; King & Spalding ILP

(57) ABSTRACT

PKC V5 isozyme-specific peptides are described. The sequences and compositions comprising the sequences are useful for treating disease states associated with the PKC isozyme from which they are respectively derived. Methods of treatment, pharmaceutical formulations and methods of identifying compounds that mimic the activity of the peptides are also described.

5 Claims, No Drawings

PEPTIDE INHIBITORS OF PROTEIN KINASE C

CROSS-REFERENCE TO RELATED APPLICATIONS

This application claims the benefit of provisional application 60/374,530, filed Apr. 22, 2002, incorporated herein by reference.

STATEMENT REGARDING GOVERNMENT INTEREST

This work was supported in part by The National Institutes of Health Grants NS13108 and DA08256. Accordingly the United States government may have certain rights in this invention.

FIELD OF THE INVENTION

The present invention relates to peptides effective for the isozyme-specific modulation of protein kinase C.

BACKGROUND OF THE INVENTION

Protein kinase C ("PKC") is a key enzyme in signal transduction involved in a variety of cellular functions, including cell growth, regulation of gene expression, and ion channel activity. The PKC family of isozymes includes at least 11 different protein kinases that can be divided into at least three subfamilies based on their homology and sensitivity to activators. Each isozyme includes a number of homologous ("conserved" or "C") domains interspersed with isozyme-unique ("variable" or "V") domains. Members of the "classical" or "cPKC" subfamily, $\alpha$, $\beta_I$, $\beta_{II}$ and $\gamma$PKC, contain four homologous domains (C1, C2, C3 and C4) and require calcium, phosphatidylserine, and diacylglycerol or phorbol esters for activation. Members of the "novel" or "nPKC" subfamily, $\delta$, $\epsilon$, $\eta$ and $\theta$PKC, lack the C2 homologous domain and do not require calcium for activation. Finally, members of the "atypical" or "aPKC" subfamily, $\zeta$ and $\lambda$/lPKC, lack both the C2 and one-half of the C1 homologous domains and are insensitive to diacylglycerol, phorbol esters and calcium.

Studies on the subcellular distribution of PKC isozymes demonstrate that activation of PKC results in its redistribution in the cells (also termed translocation), such that activated PKC isozymes associate with the plasma membrane, cytoskeletal elements, nuclei, and other subcellular compartments (Saito, N. et al., *Proc. Natl. Acad. Sci. USA* 86:3409-3413 (1989); Papadopoulos, V. and Hall, P. F. *J. Cell Biol.* 108:553-567 (1989); Mochly-Rosen, D., et al., *Molec. Biol. Cell* (formerly *Cell Reg.*) 1:693-706, (1990)). The unique cellular functions of different PKC isozymes are determined by their subcellular location. For example, activated $\beta_I$PKC is found inside the nucleus, whereas activated $\beta_{II}$PKC is found at the perinucleus and cell periphery of cardiac myocytes (Disatnik, M. H., et al., *Exp. Cell Res.* 210:287-297 (1994)). $\epsilon$PKC, a member of the novel PKC family independent from calcium but requiring phospholipids for activation, is found in primary afferent neurons both in the dorsal root ganglia as well as in the superficial layers of the dorsal spinal cord.

The localization of different PKC isozymes to different areas of the cell in turn appears due to binding of the activated isozymes to specific anchoring molecules termed Receptors for Activated C-Kinase ("RACKs"). RACKs are thought to function by selectively anchoring activated PKC isozymes to their respective subcellular sites. RACKs bind only fully activated PKC and are not necessarily substrates of the enzyme. Nor is the binding to RACKs mediated via the catalytic domain of the kinase (Mochly-Rosen, D., et al., *Proc. Natl. Acad. Sci. USA* 88:3997-4000 (1991)). Translocation of PKC reflects binding of the activated enzyme to RACKs anchored to the cell particulate fraction and the binding to RACKs is required for PKC to produce its cellular responses (Mochly-Rosen, D., et al., *Science* 268:247-251 (1995)). Inhibition of PKC binding to RACKs in vivo inhibits PKC translocation and PKC-mediated function (Johnson, J. A., et al., *J. Biol. Chem.*, 271:24962-24966 (1996a); Ron, D., et al., *Proc. Natl. Acad. Sci. USA* 92:492-496 (1995); Smith, B. L. and Mochly-Rosen, D., *Biochem. Biophys. Res. Commun.*, 188:1235-1240 (1992)).

In general, translocation of PKC is required for proper function of PKC isozymes. Peptides that mimic either the PKC-binding site on RACKs (Mochly-Rosen, D., et al., *J. Biol. Chem.*, 226:1466-1468 (1991a); Mochly-Rosen, D., et al., 1995) or the RACK-binding site on PKC (Ron, et al., 1995; Johnson, J. A., et al., 1996a) are isozyme-specific translocation inhibitors of PKC that selectively inhibit the function of the enzyme in vivo.

Individual isozymes of PKC have been implicated in the mechanisms of various disease states, including the following: cancer (alpha and delta PKC); cardiac hypertrophy and heart failure (beta I and beta II PKC); nociception (gamma and epsilon PKC); ischemia including myocardial infarction (delta PKC); immune response, particularly T-cell mediated (theta PKC); and fibroblast growth and memory (zeta PKC). Various PKC isozyme- and variable region-specific peptides have been previously described (see, for example, U.S. Pat. No. 5,783,405). The role of $\epsilon$PKC in pain perception has recently been reported (WO 00/01415; U.S. Pat. No. 6,376, 467) including therapeutic use of the $\epsilon$V1-2 peptide (a selective inhibitor of $\epsilon$PKC first described in the above-referenced '405 patent). The binding specificity for RACK1, a selective anchoring protein for $\beta_{II}$PKC, has recently been reported to reside in the V5 region of $\beta_{II}$PKC (Stebbins, E. et al., *J. Biol. Chem.* 271:29644-29650 (2001)), including the testing of certain N-, middle, and C-terminus peptides alone, in combination and together with a mixture of three peptides from the $\beta$C2 domain.

Notwithstanding such reported advances, new, selective agents and methods for the treatment of disease, including alternatives to known PKC isozyme- and variable region-specific peptides have and continue to be desired.

SUMMARY OF THE INVENTION

The present invention provides PKC V5 isozyme-specific peptides, pharmaceutical compositions and methods for the treatment of diseases modulated by a PKC isozyme. The peptides are selective modulators of the corresponding PKC isozymes.

In one aspect the invention pertains to a PKC V5 isozyme-specific peptide.

In another aspect of the invention, the peptide is selected from 6 to 12 of the N-terminal 15 amino acids of the V5 domain.

In still another aspect the peptide does not include the N-terminal 2 amino acids of the V5 domain.

In yet another aspect, the peptide has 6 to 8 amino acids.

Still another aspect of the invention pertains to an above-described peptide conjugated to a carrier peptide, preferably Cys-Cys bonded to a carrier peptide selected from poly-Arg, Tat, or the *Drosophila* Antennapedia homeodomain.

The invention further provides pharmaceutical formulations including a pharmaceutically acceptable excipient and an above-described peptide or peptide/carrier conjugate.

The above-referenced peptides, peptide conjugates and pharmaceutical formulations include all modifications, derivations, fragments, combinations, or hybrids thereof that retain the desired activity. Excluded from the peptides of the invention are: SEQ ID NO:5, SEQ ID NO:11, SEQ ID NO:12, SEQ ID NO:13, SEQ ID NO:19, SEQ ID NO:20, SEQ ID NO:21, SEQ ID NO:31, SEQ ID NO:37, SEQ ID NO:43, SEQ ID NO:48, SEQ ID NO:57, SEQ ID NO:63 and SEQ ID NO:64.

Also provided in the present invention is a method of treatment for a disease state modulated by a PKC isozyme comprising administering a therapeutically effective amount of an above-described PKC V5 isozyme-specific peptide, peptide/carrier conjugate (or a modification, derivation, fragment, combination, or hybrid thereof that retains the desired activity) or a pharmaceutical formulation thereof to a mammal in need of such treatment. In one embodiment, excluded from the methods of treatment of the invention are those methods employing a peptide of SEQ ID NO:11, SEQ ID NO:12, SEQ ID NO:13, SEQ ID NO:19, SEQ ID NO:20, or SEQ ID NO:21. In another such embodiment, excluded from the methods of treatment of the invention are those methods employing a peptide of SEQ ID NO:5, SEQ ID NO:11, SEQ ID NO:12, SEQ ID NO:13, SEQ ID NO:19, SEQ ID NO:20, SEQ ID NO:21, SEQ ID NO:31, SEQ ID NO:37, SEQ ID NO:43, SEQ ID NO:48, SEQ ID NO:57, SEQ ID NO:63 or SEQ ID NO:64.

In another aspect, the invention includes the use of the peptides described herein to identify compounds that treat disease.

An additional aspect includes the use of a peptides or peptide/carrier conjugate in the preparation of a medicament for use in the treatment of disease.

These and other objects and features of the invention will be more fully appreciated when the following detailed description of the invention is read in conjunction with the accompanying sequences.

BRIEF DESCRIPTION OF THE SEQUENCES

SEQ ID NO:1 represents the V5 domain of the human αPKC isozyme.
SEQ ID NO:2 is a fragment derived from SEQ ID NO:1.
SEQ ID NO:3 is a modified fragment derived from SEQ ID NO:1.
SEQ ID NO:4 is a modified fragment derived from SEQ ID NO:1.
SEQ ID NO:5 is a fragment derived from SEQ ID NO:1.
SEQ ID NO:6 represents the V5 domain of the human $β_I$PKC isozyme.
SEQ ID NO:7 is a fragment derived from SEQ ID NO:6.
SEQ ID NO:8 is a fragment derived from SEQ ID NO:6.
SEQ ID NO:9 is a modified fragment derived from SEQ ID NO:6.
SEQ ID NO:10 is a modified fragment derived from SEQ ID NO:6.
SEQ ID NO:11 is a fragment derived from SEQ ID NO:6.
SEQ ID NO:12 is a fragment derived from SEQ ID NO:6.
SEQ ID NO:13 is a fragment derived from SEQ ID NO:6.
SEQ ID NO:14 represents the V5 domain of the human $β_{II}$PKC isozyme.
SEQ ID NO:15 is a fragment derived from SEQ ID NO:14.
SEQ ID NO:16 is a fragment derived from SEQ ID NO:14.
SEQ ID NO:17 is a fragment derived from SEQ ID NO:14.
SEQ ID NO:18 is a modified fragment derived from SEQ ID NO:14.
SEQ ID NO:19 is a fragment derived from SEQ ID NO:14.
SEQ ID NO:20 is a fragment derived from SEQ ID NO:14.
SEQ ID NO:21 is a fragment derived from SEQ ID NO:14.
SEQ ID NO:22 represents the V5 domain of the human γPKC isozyme.
SEQ ID NO:23 is a fragment derived from SEQ ID NO:22.
SEQ ID NO:24 is a fragment derived from SEQ ID NO:22.
SEQ ID NO:25 is a modified fragment derived from SEQ ID NO:22.
SEQ ID NO:26 represents the V5 domain of the human δPKC isozyme.
SEQ ID NO:27 is a fragment derived from SEQ ID NO:26.
SEQ ID NO:28 is a fragment derived from SEQ ID NO:26.
SEQ ID NO:29 is a modified fragment derived from SEQ ID NO:26.
SEQ ID NO:30 is a modified fragment derived from SEQ ID NO:26.
SEQ ID NO:31 is a fragment derived from SEQ ID NO:26.
SEQ ID NO:32 represents the V5 domain of the human εPKC isozyme.
SEQ ID NO:33 is a fragment derived from SEQ ID NO:32.
SEQ ID NO:34 is a fragment derived from SEQ ID NO:32.
SEQ ID NO:35 is a modified fragment derived from SEQ ID NO:32.
SEQ ID NO:36 is a modified fragment derived from SEQ ID NO:32.
SEQ ID NO:37 is a fragment derived from SEQ ID NO:32.
SEQ ID NO:38 represents the V5 domain of the human ηPKC isozyme.
SEQ ID NO:39 is a fragment derived from SEQ ID NO:38.
SEQ ID NO:40 is a fragment derived from SEQ ID NO:38.
SEQ ID NO:41 is a modified fragment derived from SEQ ID NO:38.
SEQ ID NO:42 is a modified fragment derived from SEQ ID NO:38.
SEQ ID NO:43 is a fragment derived from SEQ ID NO:38.
SEQ ID NO:44 represents the V5 domain of the human ιPKC isozyme.
SEQ ID NO:45 is a fragment derived from SEQ ID NO:44.
SEQ ID NO:46 is a fragment derived from SEQ ID NO:44.
SEQ ID NO:47 is a modified fragment derived from SEQ ID NO:44.
SEQ ID NO:48 is a fragment derived from SEQ ID NO:44.
SEQ ID NO:49 represents the V5 domain of the human μPKC isozyme.
SEQ ID NO:50 is a fragment derived from SEQ ID NO:49.
SEQ ID NO:51 is a fragment derived from SEQ ID NO:49.
SEQ ID NO:52 is a modified fragment derived from SEQ ID NO:49.
SEQ ID NO:53 represents the V5 domain of the human θPKC isozyme.
SEQ ID NO:54 is a fragment derived from SEQ ID NO:53.
SEQ ID NO:55 is a fragment derived from SEQ ID NO:53.
SEQ ID NO:56 is a modified fragment derived from SEQ ID NO:53.
SEQ ID NO:57 is a fragment derived from SEQ ID NO:53.
SEQ ID NO:58 represents the V5 domain of the human ιPKC isozyme.
SEQ ID NO:59 is a fragment derived from SEQ ID NO:58.
SEQ ID NO:60 is a fragment derived from SEQ ID NO:58.
SEQ ID NO:61 is a modified fragment derived from SEQ ID NO:58.
SEQ ID NO:62 is a modified fragment derived from SEQ ID NO:58.
SEQ ID NO:63 is a fragment derived from SEQ ID NO:58.

SEQ ID NO:64 represents a fragment derived from the V5 domain of the human μPKC isozyme.

SEQ ID NO:65 is a Tat-derived carrier peptide (Tat 47-57): Tyr Gly Lys Lys Arg Arg Gln Arg Arg Arg.

SEQ ID NO:66 is the *Drosophila* Antennapedia homeodomain-derived carrier peptide: Cys Arg Gln Ile Lys Ile Trp Phe Gln Asn Arg Arg Met Lys Trp Lys Lys.

DETAILED DESCRIPTION OF THE INVENTION

Definitions

Unless otherwise indicated, all terms herein have the same meaning as they would to one skilled in the art of the present invention. Practitioners are particularly directed to *Current Protocols in Molecular Biology* (Ausubel, F. M. et al., John Wiley and Sons, Inc., Media Pa.) for definitions and terms of the art.

Abbreviations for amino acid residues are the standard 3-letter and/or 1-letter codes used in the art to refer to one of the 20 common L-amino acids.

A "conserved set" of amino acids refers to a contiguous sequence of amino acids that is identical or closely homologous (e.g., having only conservative amino acid substitutions) between members of a group of proteins. A conserved set may be anywhere from two to over 50 amino acid residues in length. Typically, a conserved set is between two and ten contiguous residues in length. For example, for the two peptides CGRNAE(SEQ ID NO:15) and ACGRNAE(SEQ ID NO:19), there are 6 identical positions (CGRNAE) that form the conserved set of amino acids for these two sequences.

"Conservative amino acid substitutions" are substitutions that do not result in a significant change in the activity or tertiary structure of a selected polypeptide or protein. Such substitutions typically involve replacing a selected amino acid residue with a different residue having similar physico-chemical properties. For example, substitution of Glu for Asp is considered a conservative substitution since both are similarly-sized negatively-charged amino acids. Groupings of amino acids by physico-chemical properties are known to those of skill in the art.

"Domain" and "region" are used interchangeably herein and refer to a contiguous sequence of amino acids within a PKC isozyme, typically characterized by being either conserved or variable.

"Peptide" and "polypeptide" are used interchangeably herein and refer to a compound made up of a chain of amino acid residues linked by peptide bonds. Unless otherwise indicated, the sequence for peptides is given in the order from the "N" (or amino) termiums to the "C" (or carboxyl) terminus.

Two amino acid sequences or two nucleotide sequences are considered "homologous" (as this term is preferably used in this specification) if they have an alignment score of >5 (in standard deviation units) using the program ALIGN with the mutation gap matrix and a gap penalty of 6 or greater (Dayhoff, M. O., in ATLAS OF PROTEIN SEQUENCE AND STRUCTURE (1972) Vol. 5, National Biomedical Research Foundation, pp. 101-110, and Supplement 2 to this volume, pp. 1-10.) The two sequences (or parts thereof) are more preferably homologous if their amino acids are greater than or equal to 50%, more preferably 70%, still more preferably 80%, identical when optimally aligned using the ALIGN program mentioned above.

A peptide or peptide fragment is "derived from" a parent peptide or polypeptide if it has an amino acid sequence that is homologous to the amino acid sequence of, or is a conserved fragment from, the parent peptide or polypeptide.

"Modulate" intends a lessening, an increase, or some other measurable change in PKC activation.

"Management," for example in the context of treating pain, intends both a lessening of pain and/or induction of analgesia.

The term "treatment" or "treating" means any treatment of disease in a mammal, including: (a) preventing or protecting against the disease, that is, causing the clinical symptoms not to develop; (b) inhibiting the disease, that is, arresting or suppressing the development of clinical symptoms; and/or (c) relieving the disease, that is, causing the regression of clinical symptoms. It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" as defined herein. The term "protection," as used herein, is meant to include "prophylaxis."

The term "effective amount" means a dosage sufficient to provide treatment for the disorder or disease state being treated. This will vary depending on the patient, the disease and the treatment being effected.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

PKC Peptides of the Invention

Prior reports have focused on PKC isozyme- and variable region-specific peptides from the V1, V3 and V5 domains, but the therapeutic and related potentials of peptides from the V5 domain remain largely unidentified. Moreover, to the extent that peptides from the V5 domain have been described, such peptides have been predominantly selected from the approximate center of the V5 domain, starting about 25 amino acids from the N-terminus of the V5 domain.

Generally, the invention contemplates use of a peptide derived from a V5 region of any protein kinase C isozyme for use in treating and/or managing disease. The present invention pertains to such PKC isozyme-specific V5 peptides, including methods of use and treatment, compositions of matter, and pharmaceutical formulations thereof. In particular, preferred are peptides selected from about 6 to 12 of the N-terminal 15 amino acids of the V5 domain, or a conservative modification or juxtaposition thereof. Further preferred are those peptides that do not include the N-terminal 2 amino acids of the V5 domain, especially peptides having 6 to 8 amino acids. The peptides can be used in native form or modified by conjugation to a carrier, for example via a disulfide bond between a Cys on the carrier and a Cys within or added to the peptide, such as those described below.

It will be appreciated that peptides homologous to the native sequences and peptides having conservative amino acid substitutions and/or juxtapositions, as well as fragments that retain activity, are within the scope of peptides contemplated. For example, one or more amino acids (preferably no more than two) can be substituted, changing between R and K; between V, L, I, R and D; and/or between G, A, P and N. Thus, the term "a PKC V5 peptide" contemplates the native sequence and all modifications, derivations, fragments, combinations, and hybrids thereof that retain the desired activity.

The following sequences correspond to the V5 domain of various PKC isozymes and to exemplary fragments derived therefrom. Exemplary modified peptides are also described below, where the substitution(s) are indicated in lower case. In all cases, it is appreciated that sequences derived from and homologous to those expressly indicated herein (e.g., closely homologous sequences from other species) are contemplated. All peptides described herein can be prepared by chemical synthesis using either automated or manual solid phase synthetic technologies, known in the art. The peptides can also be prepared recombinantly, using techniques known in the art.

The V5 domain of the αPKC isozyme has the amino acid sequence: "PKVCG KGAENFDKFF TRGQPVLTPP DQLVIANIDQ SDFEGFSYVN PQFVHPILQS AV" (SEQ ID NO:1), which corresponds to the sequence of amino acids beginning at amino acid residue 616 of αPKC. Exemplary peptides include GKGAEN (SEQ ID NO:2), corresponding to amino acid residues 620-625, and modified peptides "arGAEN" (SEQ ID NO:3) and cGKGAEN (SEQ ID NO:4). Excluded is the peptide QLVIAN (SEQ ID NO:5).

The V5 domain of the β$_I$PKC isozyme has the amino acid sequence: "PK ARDKRDTSNF DKEFTRQPVE LTPTD-KLFIM NLDQNEFAGF SYTNPEFVIN V" (SEQ ID NO:6). Exemplary peptides include RDKRDTS (SEQ ID NO:7) and ARDKRDTSNF DK (SEQ ID NO:8), and modified peptides cARDKRDTS (SEQ ID NO:9) and gRDKRDTS (SEQ ID NO:10). Excluded are the peptides ARDKRDTS (SEQ ID NO:11), KLFIMN (SEQ ID NO:12) and AGFSYTNPEF VINV (SEQ ID NO:13).

The V5 domain of the βII-PKC isozyme has the amino acid sequence: "PK ACGRNAENFD RFFTRHPPVL TPP-DQEVIRN IDQSEFEGFS FVNSEFLKPE VKS" (SEQ ID NO:14). Exemplary peptides include CGRNAE (SEQ ID NO:15), KACGRNAE (SEQ ID NO:16) and CGRNAEN (SEQ ID NO:17) and modified peptide ACGkNAE (SEQ ID NO:18). Excluded are the peptides ACGRNAE (SEQ ID NO:19) QEVIRN (SEQ ID NO:20) and SFVNSEFLKP EVKS (SEQ ID NO:21).

The V5 domain of the γPKC isozyme has the amino acid sequence: "PRPCGRSG ENFDKFFTRA APALTPPDRL VLASIDQADF QGFTYVNPDF VHPDARSPTS PVPVPVM" (SEQ ID NO:22) taken from amino acid residue 633 et seq. of ιPKC. Exemplary are the peptides GRSGEN (SEQ ID NO:23) and PCGRSGEN (SEQ ID NO:24), and modified peptide GkSGEN (SEQ ID NO:25).

The V5 domain of the δPKC isozyme has the amino acid sequence: "PKVKSPRDY SNFDQEFLNE KARLSYSDKN LIDSMDQSAF AGFSFVNPKF EHLLED" (SEQ ID NO:26). Exemplary peptides include VKSPRDYS (SEQ ID NO:27) taken from amino acid residues 624-631, PKVK-SPRDY SN (SEQ ID NO:28), and modified peptides VKSPcRDYS (SEQ ID NO:29) and iKSPRIYS (SEQ ID NO:30). Excluded is the peptide KNLIDS (SEQ ID NO:31).

The V5 domain of the εPKC isozyme has the amino acid sequence: "PRIK TKRDVNNFDQ DFTREEPVLT LVDEAIVKQI NQEEFKGFSY FGEDLMP" (SEQ ID NO:32). Exemplary peptides include IKTKRDV (SEQ ID NO:33) taken from amino acid residues 689-695, and TKRD-VNNFDQ (SEQ ID NO:34), and modified peptides cEAIVKQ (SEQ ID NO:35) and IKTKRli (SEQ ID NO:36). Excluded is the peptide EAIVKQ (SEQ ID NO:37).

The V5 domain of the ηPKC isozyme has the amino acid sequence: "PRIKSREDV SNFDPDFIKE EPVLTPIDEG HLPMINQDEF RNFSYVSPEL QP" (SEQ ID NO:38). Exemplary peptides include IKSREDVS (SEQ ID NO:39) taken from amino acid residues 634-641, and PRIKSREDV (SEQ ID NO:40), and modified peptides vrSREDVS (SEQ ID NO:41) and EGHdPM (SEQ ID NO:42). Excluded is the peptide EGHLPM (SEQ ID NO:43).

The V5 domain of the ιPKC isozyme has the amino acid sequence: "PNISGEFGL DNFDSQFTNE PVQLTPDDDD IVRKIDQSEF EGFEYINPLL MSAEECV" (SEQ ID NO:44). Exemplary peptides include ISGEFGLD (SEQ ID NO:45) taken from amino acid resides 534-541 and DDDI-VRK (SEQ ID NO:46), and modified peptide cSGEFGLD (SEQ ID NO:47). Excluded is the peptide DDIVRK (SEQ ID NO:48).

The V5 domain of the μPKC isozyme has the amino acid sequence: "PQVKLCDFGF ARIIGEKSFR RSVVGTPAYL APEVLRNKGY NRSLDMWSVG VIIYVSLSGT FPFNEDEDIH DQIQNAAFMY PPNPWKEISH EAID-LINNLL QVKMRKRYSV DKTLSHPWLQ DYQTWLD-LRE LECKIGERYI THESDDLRWE KYAGEQRLQY PTHLINPSAS HSDTPETEET EMKALGERVS IL" (SEQ ID NO:49). Exemplary peptides include VKLCDFGF (SEQ ID NO:50) taken from amino acid resides 723-730, and QVKLCDFGFA (SEQ ID NO:51), and modified peptide irL-CDFaF (SEQ ID NO:52).

The V5 domain of the θPKC isozyme has the amino acid sequence: "PKVKSPFD CSNFDKEFLN EKPRLSFADR ALINSMDQNM FRNFSFMNPG MERLIS" (SEQ ID NO:53). Exemplary peptides include VKSPFDCS (SEQ ID NO:54) taken from amino acid resides 655-662, and DRA-LINS (SEQ ID NO:55), and modified peptides VrSPFDCS (SEQ ID NO:56). Excluded is the peptide RALINS (SEQ ID NO:57).

The V5 domain of the ζPKC isozyme has the amino acid sequence: "PQIT DDYGLDNFDT QFTSEPVQLT PDDE-DAIKRI DQSEFEGFEY INPLLLSTEE SV" (SEQ ID NO:58). Exemplary peptides include ITDDYGLD (SEQ ID NO:59) taken from amino acid resides 539-546, and DDYGLDN (SEQ ID NO:60), and modified peptides ITTDYGdl (SEQ ID NO:61) and EDAIR (SEQ ID NO:62). Excluded is the peptide EDAIKR (SEQ ID NO:63). Also excluded is the peptide SDSPEA (SEQ. ID NO:64), identified as μPKC V5 peptide "μV51" in U.S. Pat. No. 5,783,405.

In all of the exemplary fragments recited above, conservative modifications and other modifications that do not appreciably alter the activity can be made and fall within the contemplated peptides.

Preferred are the peptides of the group: SEQ ID NO:2, SEQ ID NO:3, SEQ ID NO:4, SEQ ID NO:7, SEQ ID NO:8, SEQ ID NO:9, SEQ ID NO:10, SEQ ID NO:15, SEQ ID NO:16, SEQ ID NO:17, SEQ ID NO:18, SEQ ID NO:23, SEQ ID NO:24, SEQ ID NO:25, SEQ ID NO:27, SEQ ID NO:28, SEQ ID NO:29, SEQ ID NO:30, SEQ ID NO:33, SEQ ID NO:34, SEQ ID NO:35, SEQ ID NO:36, SEQ ID NO:39, SEQ ID NO:40, SEQ ID NO:41, SEQ ID NO:42, SEQ ID NO:45, SEQ ID NO:46, SEQ ID NO:47, SEQ ID NO:50, SEQ ID NO:51, SEQ ID NO:52, SEQ ID NO:54, SEQ ID NO:55, SEQ ID NO:56, SEQ ID NO:59, SEQ ID NO:60, SEQ ID NO:61 and SEQ ID NO:62, optionally including all modifications, derivations, fragments, combinations, and hybrids thereof that retain the desired activity.

More preferred are the peptides of the group: SEQ ID NO:2, SEQ ID NO:7, SEQ ID NO:8, SEQ ID NO:15, SEQ ID NO:16, SEQ ID NO:17, SEQ ID NO:23, SEQ ID NO:24, SEQ ID NO:27, SEQ ID NO:28, SEQ ID NO:33, SEQ ID NO:34, SEQ ID NO:39, SEQ ID NO:40, SEQ ID NO:45, SEQ ID NO:46, SEQ ID NO:50, SEQ ID NO:51, SEQ ID NO:54, SEQ ID NO:55, SEQ ID NO:59 and SEQ ID NO:60, optionally including all modifications, derivations, fragments, combinations, and hybrids thereof that retain the desired activity.

Still more preferred are the peptides of the group: SEQ ID NO:2, SEQ ID NO:7, SEQ ID NO:15, SEQ ID NO:23, SEQ ID NO:27, SEQ ID NO:33, SEQ ID NO:39, SEQ ID NO:45, SEQ ID NO:50, SEQ ID NO:54 and SEQ ID NO:59, optionally including all modifications, derivations, fragments, combinations, and hybrids thereof that retain the desired activity.

Similarly preferred are the peptides of the group: SEQ ID NO:2, SEQ ID NO:23, SEQ ID NO:27, SEQ ID NO:33, SEQ ID NO:39, SEQ ID NO:45, SEQ ID NO:50, SEQ ID NO:54 and SEQ ID NO:59, optionally including all modifications, derivations, fragments, combinations, and hybrids thereof that retain the desired activity.

Utility

Therapeutic Indications

The PKC isozyme-specific V5 peptides of the present invention are useful as modulators of PKC, being selective for the isozyme from which they are derived. In that regard, the peptides can be used in the treatment of mammalian (especially human) disease states associated with particular PKC isozymes, including: αPKC (hyperproliferative cellular diseases, such as cancer); $β_I$PKC and $β_{II}$PKC (cardiac hypertrophy and heart failure); γPKC (pain management); δPKC (protecting tissue from damage due to an ischemic or hypoxic event, such as myocardial infarction and stroke, or apoptosis induced by UV irradiation, and for inhibiting fibroblast growth to promote scarless wound healing); εPKC (pain management, myocardial dysfunction); θPKC (immune system modulation, particularly involving T-cell mediated responses); and ζPKC (memory and stimulating fibroblast growth).

By way of example, pain is a basic clinical symptom seen by physicians and is often categorized as mild, moderate, or severe. The γPKC and εPKC peptides described herein are suitable for treatment of pain in any of these categories. For example, cancer and post-operative surgical pain are often described as being in the moderate-to-severe category. Tumor infiltration of bone, nerve, soft tissue, or viscera are common causes of cancer pain. Various factors influence the prevalence of cancer pain in patients, such as the tumor type, state, and site, as well as patient variables. With respect to post-operative pain, the severity of the pain is often dependent on location and extent of intervention.

More particularly, the γPKC and εPKC peptides are suited to treatment of acute or chronic pain caused, for example, by neuropathic or inflammatory conditions. Exemplary inflammatory conditions contemplated for treatment include, but are not limited to, sunburn, osteoarthritis, colitis, carditis, dermatitis, myostis, neuritis, and rheumatoid arthritis, lupus and other collagen vascular diseases, as well as post-operative surgical pain. Conditions associated with neuropathic pain include, but are not limited to, trauma, surgery, amputation, abscess, demyelinating diseases, trigeminal neuralgia, cancer, chronic alcoholism, stroke, thalamic pain syndrome, diabetes, herpes infections, and the like.

Inflammation and nerve damage can induce hyperalgesia, where a noxious stimulus is perceived as intensely painful due to a lowering of pain threshold. Accordingly, in its embodiments addressed to the treatment of pain, the invention contemplates a composition and a method for treating hyperalgesia in a patient. Additionally, the invention contemplate compositions and methods for treating allodynia in a subject; that is, treating the pain associated with a normally non-noxious stimulus.

Use in Methods of Identification

Another aspect the usefulness of the invention is a method of identifying compounds that modulate pain, for example, by using the peptides described herein as research tools for identification of compounds that mimic the activity of the peptides. The invention also contemplates use of the peptides in assays to detect the site of action of the peptides or in studies on the mechanism of action of the peptides. In identifying compounds that mimic the activity of the peptides, compounds that are able to bind to cellular receptors to which the peptides bind or otherwise act in the same of a similar physiological manner as the peptides can be identified by several techniques. For example, one method comprises adding a test compound to a biological assay that determines the activity of a PKC peptide of the invention and detecting the activity of the test compound. Alternatively, test compounds that modulate the activity of a PKC isozyme can be determined with an assay and then tested for a corresponding therapeutic activity.

For example, a competitive binding screening assay can be used to identify compounds that mimic the activity of a PKC isozyme by adding a test compound and a detectably labeled peptide of the invention to mammalian cells, tissue, or the suitable RACK under conditions that allow binding of the peptide and comparing the results against binding of the labeled peptide (without test compound) to the cell, tissue or RACK. Compounds that mimic the activity of the peptide can compete with the peptide for binding to the cell, tissue or RACK. Consequently, a smaller amount of RACK-bound labeled peptide (or a larger amount of RACK-unbound labeled peptide) will be measured when the test compound mimics the activity of the peptide by binding to the receptor (as compared to the amounts of free and RACK-bound labeled peptide when a test compound does not mimic the activity of the peptide, does not bind to the receptor, or does so with less affinity).

In general, identification of compounds that mimic the activity of PKC isozymes are identified by measuring the ability of a test compound to inhibit, enhance, or modulate the activity of the corresponding PKC isozyme. The activity of the PKC isozyme in a selected assay is measured in the presence and absence of the test compound. The assay can be a competitive binding assay (e.g., as described above) or a cellular assay the monitors modulation of a second messenger production, changes in cellular metabolism, or effects on enzymatic activity. Compounds identified as mimicking or modulating the activity of the PKC isozyme are then tested for therapeutic activity using a corresponding in vivo disease model.

Testing

Activity of the peptides of the invention can be determined using any of the established in vitro and in vivo assays of efficacy in treatment of the above-mentioned indications. Ultimately, of course, safety and efficacy are determined in controlled human clinical studies.

Representative testing protocols are summarized below in the context of determining activity for the treatment of pain, and for the treatment of ischemia. Testing protocols for other PKC V5 peptide indications will be well known to those skilled in the art.

V5 Domain Activity as Illustrated by PKC Peptides for Pain Management

The effect of a PKC peptide to modulate nociception is investigated using models of acute inflammatory pain induced by capsaicin or by formalin. These models, and others, having long-term increases of sensitivity to noxious stimuli can be useful in modeling certain human pathological pain. The capsaicin model of inflammation, together with a low rate thermal test, mimics central sensitization and hyperalgesia resulting from chronic pain. Application of capsaicin to the skin produces a robust, hours-long, C fiber selective hyperalgesia indicated by significant lowering of paw withdrawal latencies during low heating rate thermal tests. Capsaicin is the active ingredient in spicy "hot" foods. The receptor for capsaicin (VR-1 vanilloid receptor found on C fibers) has been recently cloned. It is a ligand-gated, non-selective cation channel. In addition to responding to capsaicin, VR-1 also responds to thermal stimuli (approximately 43° C.) (Kidd B. L., et al., Br. J. Anaesth., 87(1):3-11 (2001)) and to protons, suggesting that its activity is enhanced during inflammation. Capsaicin has been shown to selectively activate and sensitize C fibers, and not Aδ. Therefore, Aδ latency measurements are used as controls for animal wellbeing during the studies.

The formalin model in rodents has been validated as a predictive test of treating injury-induced pain in humans (Dennis, S. G. and Melzack, R. in Advances in Pain Research and Therapy, Vol. 3, 747, Eds. J. J. Bonica et al., Raven Press, New York, 1979; Tjolsen, A., et al., Pain, 51:5-17 (1992)). The model produces a bi-phasic response, where the initial phase is triggered by a primary afferent barrage, similar in character to that described for the acute phasic tests except that chemical nociceptors are the mediators. The second phase is considered to be the hyperalgesic spontaneous activity that results from the initial tissue damage and reflects the lowering of nociceptive threshold plus the priming or "wind up" of the corresponding spinal circuitry. Thus, both peripheral and central neuronal circuits and mediators are required to induce and sustain this painful tissue-injury condition.

When tested as described above, γPKC V5 peptides and εPKC V5 peptides confer a substantial reduction in pain.

V5 Domain Activity as Illustrated by PKC Peptides for Ischemia

Administration to isolated rat cardiac myocytes can be employed to determine the activity of δPKC peptides in protection from ischemia. A peptide or carrier-peptide conjugate is introduced into isolated adult rat cardiac myocytes ten minutes prior to prolonged ischemia. Cell damage is assessed using an osmotic fragility test by measuring uptake of trypan blue.

Administration to whole hearts ex vivo can be employed to determine if the peptides have activity when introduced extracellulary to a whole organ. Peptides optionally conjugated to a carrier peptide, a Tat-derived peptide are delivered into Langendorff perfused rat hearts prior to induction of an ischemic period. After perfusion with the peptides, global ischemia is effected for 30 minutes. After the 30 minute ischemic period, the amount of creatine phosphokinase (CPK) released is monitored during a 30 minute reperfusion period.

Another study determines if the peptides can be delivered to an intact organ to provide protection after an ischemic insult. In this study, the rat heart model described above is used and the hemodynamic parameters are measured during the 20 minutes of global ischemia and the 20 minutes of reperfusion. Test peptides are delivered at a concentration of 500 nM, only during the reperfusion period.

Protecting tissue from damage due to an ischemic or hypoxic event can be evaluated by administering the peptide in vivo to adult female pigs, preferably during the last 10 minutes of a 30 minute ischemic insult. Five days later, the hearts are analyzed for tissue damage.

In another study, left ventricurogram is performed in pigs (n=5) at three time points: (1) before occlusion of left anterior descending artery by balloon catheter (pre ischemia); (2) immediately after reperfusion with 2.5 μM/10 mL of δV1-1 (post ischemia); and (3) before sacrifice five days later (5 days post ischemia), using 6 Fr. of pig-tail catheter. LVG is recorded by 2 views, right anterior oblique and left anterior oblique. Ejection fraction (EF), the percent of blood ejected in a beat, during maximum contraction, of the total maximum present in the left ventricle, is analyzed by the software, Plus Plus (Sanders Data Systems), and the averages of two views are evaluated. Ejection fractions are calculated based on left ventricle dimensions. Ejection fraction is a measure of how well the heart is functioning, with a higher ejection fraction indicative of a better functioning heart. An ejection fraction of less than 50% in a short period of time can suggest progression into a state of heart failure.

Inhibition of damage to the brain as a result of stroke can be examined in a rat cerebral ischemia model. Ischemia is induced using an intraluminal suture to occlude the ostium of the middle cerebral artery. Test peptide, optionally conjugated to a Tat peptide or the Tat peptide alone are injected into the carotid artery before and after a two hour occlusion period. The brain from each animal is harvested 24 hours later, stained, and examined.

When tested as described above, δPKC V5 peptides, when delivered before, during, or after ischemia, confer a substantial reduction of damage to the heart and brain induced by ischemia.

Administration

The peptides are prepared for administration by combining with a pharmaceutically-acceptable carrier or diluent. Thus, a further aspect of the invention provides pharmaceutical compositions comprising a peptide of the invention in a dosage form for administration to a subject. Such a dosage form includes, but is not limited to, tablets, capsules, suspensions, syrups for oral administration, where suitable pharmaceutical carriers include starch, lactose, talc, magnesium stearate, aqueous solutions, oil-water emulsions, and the like. Other dosage forms include intrathecal, intravenous, intramuscular, subcutaneous, where suitable pharmaceutical carriers include buffered-aqueous or non-aqueous media. The peptides can be locally administered (e.g., near a site of inflammation or peripheral nerve damage) for example, by topical application, intradermal injection or drug delivery catheter.

The amount of the peptide in the composition can be varied so that a suitable dose is obtained and a therapeutic effect is achieved. The dosage will depend on a number of factors such as the route of administration, the duration of treatment, the size and physical condition of the patient, the potency of the peptide and the patient's response. Effective amounts of the peptide can be determined by testing the peptide in one or more models known in the art, including those described herein.

The peptides can be administered as needed, hourly, several times per day, daily, or as often as the person experiencing the pain or that person's physician deems appropriate. The peptides can be administered on an on-going basis for management of chronic indications, or can be administered on a short term basis prior to after an acute indications.

The peptides of the invention can be administered alone or linked to a carrier peptide, such as a Tat carrier peptide (of which the peptide having the sequence identified as SEQ ID NO:65 is exemplary). Other suitable carrier peptides are known and contemplated, such as the *Drosophila* Antennapedia homeodomain (SEQ ID NO:66; Théodore, L., et al. *J.*

Neurosci. 15:7158 (1995); Johnson, J. A., et al., *Circ. Res.* 79:1086 (1996b)), where the PKC peptide is cross-linked via an N-terminal Cys-Cys bond to the Antennapedia carrier. Polyarginine is another exemplary carrier peptide (Mitchell et al., *J. Peptide Res.*, 56:318-325 (2000); Rothbard et al., *Nature Med.*, 6:1253-1 257 (2000)).

EXAMPLES

The following examples further illustrate the invention described herein and are in no way intended to limit the scope of the invention.

Example 1

Effect of PKC Peptides on Capsaicin-Induced Nociception

Adult male Sprague-Dawley rats weighing between 200-250 g are lightly anaesthetized with urethane (800 mg. kg, i.p.). The dorsal surface of each animal is painted with India ink to ensure heat is applied evenly to the dorsal surface. Baseline measurements of all animals (n=10/test group) are taken for 45 minutes for both C-fibers (0.9° C./sec heating rate) and Aδ-fibers (6.5° C./sec heating rate). The peptides administered are a positive control εPKC antagonist having the amino acid sequence EAIVKQ (SEQ ID NO:37) that had previously been identified active in the assay, the γPKC peptides identified as SEQ ID NO:23, SEQ ID NO:24 and SEQ ID NO:25 and the εPKC peptides identified as SEQ ID NO:33, SEQ ID NO:33, SEQ ID NO:34, SEQ ID NO:35 and SEQ ID NO:36. All peptides are linked to a Tat carrier peptide, of which the sequenced identified as SEQ ID NO:65 is exemplary. A second series of the peptides is tested without a carrier. Control and test peptides are delivered intrathecally via direct lumbar puncture (10 μM peptide in 20 μL) 15 minutes prior to topical application of capsaicin on the left hind paw (100 μL of 3% capsaicin). As negative controls, saline and Tat-carrier peptide are also administered to two separate groups of test animals. A latency measurement is taken post peptide but prior to capsaicin application to control for direct peptide effect. Twenty minutes after the application of capsaicin, the ink is reapplied, and the dorsal surface of the hind paws is subjected to low rate heating for a maximum of 20 seconds. Foot withdrawal latencies are measured at 15 minute intervals. The εPKC and γPKC test peptides result in a decreased pain score relative to the negative control pups.

Example 2

Effect of PKC Peptides on Pre-Existing Capsaicin-Induced Nociception

Testing of the γPKC and εPKC peptides for treatment of pre-existing chronic pain is done as follows. The ability of the peptides to reverse established capsaicin-induced thermal hyperalgesia is determined using the procedure described in Example 1, except the test peptides are administered at various concentrations of test peptides (1 μM, 50 μM, and 100 μM) over a 10-minute period commencing 25 minutes post capsaicin treatment (i.e., capsaicin is administered after the baseline measurements).Thermal testing is then done as described in Example 1. Thirty minutes after capsaicin application, paw withdrawal latency was measured at regular intervals for 75 minutes. The εPKC and γPKC test peptides result in a decreased pain score relative to the negative control pups.

Example 3

Inhibition of δPKC Translocation

A. Peptide Preparation

δV5 PKC peptides (SEQ ID NO:27, SEQ ID NO:28, SEQ ID NO:29 and SEQ ID NO:30) are synthesized and purified. The peptides are modified with a carrier peptide by cross-linking via an N-terminal Cys-Cys bond to the *Drosophila* Antennapedia homeodomain (Théodore, L., et a/.; Johnson, J. A. et al., 1996b) or a Tat-derived peptide.

B. Peptide Delivery Into Cells

Primary cardiac myocyte cell cultures (90-95% pure) are prepared from newborn rats (Gray, M. O. et al.; Disatnik M.-H. et al.). The peptides are introduced into cells at an applied concentration of 500 nM in the presence and absence of phorbol 12-myristate 13-acetate (PMA) at concentrations of 3 nm and 10 nm, respectively, for 10-20 minutes. In a third set of cells, the peptides are applied at a concentration of 500 nM in the presence and absence of 500 nM ψδRACK.

Translocation of δPKC isozyme is assessed by using δPKC isozyme-specific antibodies in Western blot analysis (Santa Cruz Biotechnology). Western blot analysis of cystosolic and particulate fractions of treated cells is carried out as described by Johnson et al., 1995. Subcellular localization of delta PKC isozymes is assessed by chemiluminescence of blots probed with anti-δPKC, anti-αPKC and anti-εPKC antibodies. Amounts of PKC isozymes in each fraction are quantitated using a scanner and translocation is expressed as the amount of isozymes in the particulate fraction over the amount of isozymes in non-treated cells. Changes in translocation of δPKC isozyme are also determined by immunofluoresence study of treated and fixed cells (Gray et al., 1997). Translocation is determined by counting over 100 cells/treatment in a blinded fashion.

When tested as described above, the δV5 PKC peptides are active inhibitors of delta PKC translocation.

Example 4

Peptide Administration to Isolated Cardiac Myocytes

The peptides are prepared as described in Example 3.

Adult male Wistar rat cardiomyocytes are prepared on a Langendorff apparatus (van der Heide, R. S. et al.) by collagenase treatment (Armstrong, S. et al.). The cells are treated with peptides at concentrations of 10 nM, 100 nM, 500 nM, and 1 μM in the presence or absence of 1 μM ψδRACK. βPKC-selective activator was used as a control.

For stimulated ischemia, adult myocytes treated in microcentrifuge tubes with δV1-1 and/or ψδRACK peptides conjugated to the carrier are washed twice with degassed glucose-free incubation buffer and pelleted. On top of a minimal amount of buffer, the cell pellets are overlaid with either a micro-balloon (Sig Manufacturing, Montezuma, Iowa) or with degassed buffer satured with nitrogen, and sealed with an airtight top. Tubes are then incubated at 37° C. for either 180 minutes or 90 minutes.

Cell damage is assessed by an osmotic fragility test by measuring the uptake of trypan blue added in a hypotonic (85 mosM) solution. Similar results are also obtained by using a live-dead kit (Molecular Probes) or measuring the release of lactose dehydrogenase to the medium using a kit (Sigma) as previously described (Chen, et al., 1999; Gray et al., 1997; Mackay et al., 1999).

The δV5 PKC peptides inhibit ischemic damage when tested as described above.

Example 5

Ex Vivo Peptide Administration to Whole Hearts and Effect on Cell Damage

Adult, male rats are anesthetized with i.p. avertin, and their hearts are rapidly removed and cannulated via the aorta for perfusion as described in the art (Colbert, M. C. et al.) using Langendorff set-up. Care is taken to have the hearts perfused within 90 seconds of removal. The hearts are perfused with oxygenated Krebs-Henseleit solution comprised of, in nmol/L, NaCl 120; KCl 5.8; NaHCO$_3$ 25; NaH$_2$O$_4$ 1.2; MgSO$_4$ 1.2; CaCl$_2$ 1.0; and dextrose 10, pH 7.4 at 37° C.

After a 10-20 minute equilibration period, the hearts are perfused with δV5 PKC peptides, prepared as described in Example 1 but conjugated to a Tat-derived peptide, for 20 minutes. Perfusion is maintained at a constant flow of 10 mL/min with Krebs-Hanseleit solution containing 0.5 μM of the appropriate peptide. The Langendorff method employed uses retrograde flow from the ventricle to the aorta and into the coronary arteries, bypassing the pulmonary arteries.

To induce global ischemia, flow is interrupted for 30 minutes. After the ischemic event, the hearts are re-perfused for 30-60 minutes. During reperfusion, ischemia-induced cell damage is determined by measuring the activity of creatine phosphokinase (CPK) (absorbance at 520 nm) in the perfusate using a Sigma kit. As controls, some ex vivo hearts are left untreated, or maintained under normoxia conditions, or treated with the Tat-carrier peptide alone, or treated with Tat-carrier peptide conjugated to a previously identified inactive peptide.

The δV5 PKC peptides inhibit ischemic damage when tested as described above.

Example 6

In Vivo Administration of δV1-1 After Ischemia

Adult female pigs, 35-40 kg in weight, are anesthetized and a catheter is introduced through the carotid artery into the heart. Using conventional intervention cardiology techniques, a wire is placed through a catheter and into the left anterior descending artery. A balloon is run over this wire to a site of occlusion where it is then inflated to block blood flow for 30 minutes. During the last 10 minutes of the 30-minute occlusion, either a control comprised of a carrier peptide alone or a test peptide (optionally conjugated to a carrier Tat peptide as described above) is delivered by slow diffusion (1 mL/min) directly downstream of the occlusion. Approximately 20 μg of test peptide (~400 ng per kg body weight) is administered.

After 30 minutes of occlusion, the balloon is removed and pigs are left to recover from surgery. Five days later, the pigs are euthanized and hearts are, harvested. After heart removal, the LAD is occluded. With the occlusion in place, Evans Blue dye, which stains all areas not at risk of infarct in blue while leaving all areas with no access to blood flow red, is infused. Hearts are then cut into slices and stained with a tetrazolium red dye which stains all live areas red and infarcted dead tissue in white. Each heart has multiple tissue slices with distinctive areas marking the area at risk for ischemia and the infarcted area. From this, the percent infarct per area at risk for each slice and for the entire heart is determined.

The δV5 PKC peptides inhibit ischemic damage when tested as described above.

Example 7

In Vivo Administration to Rats for Stroke Damage Protection

A. Cerebral Ischemia Model

Adult male Sprague-Dawley rats weighing between 280-320 g are used. Animals are maintained under isofluorane anesthesia during all surgical procedures. Physiological parameters are monitored and maintained in the normal range. Rectal temperature is also measured. At the completion of the experiment, the animals are euthanized with a barbiturate overdose and prepared for histological analysis.

B. Focal Model

Ischemia is induced using an occluding intraluminal suture. An uncoated 30 mm long segment of 3-0 nylon monofilament suture with the tip rounded by flame is inserted into the stump of the common carotid artery and advanced into the internal carotid artery approximately 19-20 mm from the bifurcation in order to occlude the ostium of the middle cerebral artery. Sham control animals undergo similar anesthesia and surgical manipulation, but do not experience ischemia. At the end of a 2 hour ischemic period, the suture is removed and the animal allowed to recover. Brains are harvested after 24 hrs of reperfusion.

C. Peptide Delivery

Test peptide optionally conjugated to Tat peptide, or Tat carrier control peptide (50 μL of 10 μM solution in saline) are injected into the carotid artery either immediately before or before and after the 2 hours occlusion. The final blood concentration of test peptide is 1 μM.

D. Histology

Animals are perfused with heparinized saline and brains removed and sectioned into 2 mm thick slices. To assess ischemic injury, brain sections are stained with cresyl violet or with triphenyl tetrazolium chloride, a live tissue stain to indicate the regions of infarct. Areas of infarction (white) are then measured using an image analysis system previously described (Yenari, M. A. et al., 1998; Maier, C. et al., 1998).

The δV5 PKC peptides inhibit ischemic damage when tested as described above.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:

1. A peptide selected from the group consisting of SEQ ID NO:7, SEQ ID NO:8, SEQ ID NO:9, SEQ ID NO:10, SEQ ID NO:15, SEQ ID NO:16, SEQ ID NO:17, and SEQ ID NO:18, and wherein said peptide inhibits beta PKC isozyme activity.

2. The peptide of claim 1 wherein said peptide is modified to include a terminal cysteine amino acid residue bonded to a terminal cysteine amino acid residue on a carrier peptide selected from poly-Arg, Tat, or the *Drosophila* Antennapedia homeodomain.

3. A pharmaceutical formulation comprising a pharmaceutically acceptable excipient and a peptide of claim 1.

4. A pharmaceutical formulation comprising a pharmaceutically acceptable excipient and a peptide/carrier conjugate of claim 2.

5. A peptide of claim 2, wherein said carrier peptide is selected from SEQ ID NO:65 and SEQ ID NO:66.

* * * * *

UNITED STATES PATENT AND TRADEMARK OFFICE
CERTIFICATE OF CORRECTION

PATENT NO. : 7,507,711 B2  
APPLICATION NO. : 10/421503  
DATED : March 24, 2009  
INVENTOR(S) : Mochly-Rosen et al.

Page 1 of 1

It is certified that error appears in the above-identified patent and that said Letters Patent is hereby corrected as shown below:

In The Specification Under Column 1:

• Please replace lines 11-17 with:

--FEDERALLY SPONSORED RESEARCH OR DEVELOPMENT  
This invention was made with Government support under contracts DA008256 and NS013108 awarded by the National Institutes of Health. The Government has certain rights in this invention.--

Signed and Sealed this  
Nineteenth Day of April, 2011

David J. Kappos  
*Director of the United States Patent and Trademark Office*

SEQUENCE LISTING

<160> NUMBER OF SEQ ID NOS: 66

<210> SEQ ID NO 1
<211> LENGTH: 57
<212> TYPE: PRT
<213> ORGANISM: Artificial
<220> FEATURE:
<223> OTHER INFORMATION: V5 domain of the human alphaPKC isozyme

<400> SEQUENCE: 1

Pro Lys Val Cys Gly Lys Gly Ala Glu Asn Phe Asp Lys Phe Phe Thr
1               5                   10                  15

Arg Gly Gln Pro Val Leu Thr Pro Pro Asp Gln Leu Val Ile Ala Asn
            20                  25                  30

Ile Asp Gln Ser Asp Phe Glu Gly Phe Ser Tyr Val Asn Pro Gln Phe
        35                  40                  45

Val His Pro Ile Leu Gln Ser Ala Val
    50                  55

<210> SEQ ID NO 2
<211> LENGTH: 6
<212> TYPE: PRT
<213> ORGANISM: Artificial
<220> FEATURE:
<223> OTHER INFORMATION: fragment derived from SEQ ID NO:1

<400> SEQUENCE: 2

Gly Lys Gly Ala Glu Asn
1               5

<210> SEQ ID NO 3
<211> LENGTH: 6
<212> TYPE: PRT
<213> ORGANISM: Artificial
<220> FEATURE:
<223> OTHER INFORMATION: modified fragment derived from SEQ ID NO:1

<400> SEQUENCE: 3

Ala Arg Gly Ala Glu Asn
1               5

<210> SEQ ID NO 4
<211> LENGTH: 7
<212> TYPE: PRT
<213> ORGANISM: Artificial
<220> FEATURE:
<223> OTHER INFORMATION: modified fragment derived from SEQ ID NO:1

<400> SEQUENCE: 4

Cys Gly Lys Gly Ala Glu Asn
1               5

<210> SEQ ID NO 5
<211> LENGTH: 6
<212> TYPE: PRT
<213> ORGANISM: Artificial
<220> FEATURE:
<223> OTHER INFORMATION: fragment derived from SEQ ID NO:1

<400> SEQUENCE: 5

Gln Leu Val Ile Ala Asn
1               5

```
<210> SEQ ID NO 6
<211> LENGTH: 53
<212> TYPE: PRT
<213> ORGANISM: Artificial
<220> FEATURE:
<223> OTHER INFORMATION: V5 domain of the human beta1PKC isozyme

<400> SEQUENCE: 6

Pro Lys Ala Arg Asp Lys Arg Asp Thr Ser Asn Phe Asp Lys Glu Phe
1               5                   10                  15

Thr Arg Gln Pro Val Glu Leu Thr Pro Thr Asp Lys Leu Phe Ile Met
                20                  25                  30

Asn Leu Asp Gln Asn Glu Phe Ala Gly Phe Ser Tyr Thr Asn Pro Glu
            35                  40                  45

Phe Val Ile Asn Val
        50

<210> SEQ ID NO 7
<211> LENGTH: 7
<212> TYPE: PRT
<213> ORGANISM: Artificial
<220> FEATURE:
<223> OTHER INFORMATION: fragment derived from SEQ ID NO:6

<400> SEQUENCE: 7

Arg Asp Lys Arg Asp Thr Ser
1               5

<210> SEQ ID NO 8
<211> LENGTH: 12
<212> TYPE: PRT
<213> ORGANISM: Artificial
<220> FEATURE:
<223> OTHER INFORMATION: fragment derived from SEQ ID NO:6

<400> SEQUENCE: 8

Ala Arg Asp Lys Arg Asp Thr Ser Asn Phe Asp Lys
1               5                   10

<210> SEQ ID NO 9
<211> LENGTH: 9
<212> TYPE: PRT
<213> ORGANISM: Artificial
<220> FEATURE:
<223> OTHER INFORMATION: modified fragment derived from SEQ ID NO:6

<400> SEQUENCE: 9

Cys Ala Arg Asp Lys Arg Asp Thr Ser
1               5

<210> SEQ ID NO 10
<211> LENGTH: 8
<212> TYPE: PRT
<213> ORGANISM: Artificial
<220> FEATURE:
<223> OTHER INFORMATION: modified fragment derived from SEQ ID NO:6

<400> SEQUENCE: 10

Gly Arg Asp Lys Arg Asp Thr Ser
1               5

<210> SEQ ID NO 11
<211> LENGTH: 8
<212> TYPE: PRT
<213> ORGANISM: Artificial
```

<220> FEATURE:
<223> OTHER INFORMATION: fragment derived from SEQ ID NO:6

<400> SEQUENCE: 11

Ala Arg Asp Lys Arg Asp Thr Ser
1               5

<210> SEQ ID NO 12
<211> LENGTH: 6
<212> TYPE: PRT
<213> ORGANISM: Artificial
<220> FEATURE:
<223> OTHER INFORMATION: fragment derived from SEQ ID NO:6

<400> SEQUENCE: 12

Lys Leu Phe Ile Met Asn
1               5

<210> SEQ ID NO 13
<211> LENGTH: 14
<212> TYPE: PRT
<213> ORGANISM: Artificial
<220> FEATURE:
<223> OTHER INFORMATION: fragment derived from SEQ ID NO:6

<400> SEQUENCE: 13

Ala Gly Phe Ser Tyr Thr Asn Pro Glu Phe Val Ile Asn Val
1               5                   10

<210> SEQ ID NO 14
<211> LENGTH: 55
<212> TYPE: PRT
<213> ORGANISM: Artificial
<220> FEATURE:
<223> OTHER INFORMATION: V5 domain of the human beta2PKC isozyme

<400> SEQUENCE: 14

Pro Lys Ala Cys Gly Arg Asn Ala Glu Asn Phe Asp Arg Phe Phe Thr
1               5                   10                  15

Arg His Pro Pro Val Leu Thr Pro Pro Asp Gln Glu Val Ile Arg Asn
            20                  25                  30

Ile Asp Gln Ser Glu Phe Glu Gly Phe Ser Phe Val Asn Ser Glu Phe
        35                  40                  45

Leu Lys Pro Glu Val Lys Ser
    50                  55

<210> SEQ ID NO 15
<211> LENGTH: 6
<212> TYPE: PRT
<213> ORGANISM: Artificial
<220> FEATURE:
<223> OTHER INFORMATION: fragment derived from SEQ ID NO:14

<400> SEQUENCE: 15

Cys Gly Arg Asn Ala Glu
1               5

<210> SEQ ID NO 16
<211> LENGTH: 8
<212> TYPE: PRT
<213> ORGANISM: Artificial
<220> FEATURE:
<223> OTHER INFORMATION: fragment derived from SEQ ID NO:14

```
<400> SEQUENCE: 16

Lys Ala Cys Gly Arg Asn Ala Glu
1               5

<210> SEQ ID NO 17
<211> LENGTH: 7
<212> TYPE: PRT
<213> ORGANISM: Artificial
<220> FEATURE:
<223> OTHER INFORMATION: fragment derived from SEQ ID NO:14

<400> SEQUENCE: 17

Cys Gly Arg Asn Ala Glu Asn
1               5

<210> SEQ ID NO 18
<211> LENGTH: 7
<212> TYPE: PRT
<213> ORGANISM: Artificial
<220> FEATURE:
<223> OTHER INFORMATION: modified fragment derived from SEQ ID NO:14

<400> SEQUENCE: 18

Ala Cys Gly Lys Asn Ala Glu
1               5

<210> SEQ ID NO 19
<211> LENGTH: 7
<212> TYPE: PRT
<213> ORGANISM: Artificial
<220> FEATURE:
<223> OTHER INFORMATION: fragment derived from SEQ ID NO:14

<400> SEQUENCE: 19

Ala Cys Gly Arg Asn Ala Glu
1               5

<210> SEQ ID NO 20
<211> LENGTH: 6
<212> TYPE: PRT
<213> ORGANISM: Artificial
<220> FEATURE:
<223> OTHER INFORMATION: fragment derived from SEQ ID NO:14

<400> SEQUENCE: 20

Gln Glu Val Ile Arg Asn
1               5

<210> SEQ ID NO 21
<211> LENGTH: 14
<212> TYPE: PRT
<213> ORGANISM: Artificial
<220> FEATURE:
<223> OTHER INFORMATION: fragment derived from SEQ ID NO:14

<400> SEQUENCE: 21

Ser Phe Val Asn Ser Glu Phe Leu Lys Pro Glu Val Lys Ser
1               5                   10

<210> SEQ ID NO 22
<211> LENGTH: 65
<212> TYPE: PRT
<213> ORGANISM: Artificial
<220> FEATURE:
<223> OTHER INFORMATION: V5 domain of the human gammaPKC isozyme
```

```
-continued

<400> SEQUENCE: 22

Pro Arg Pro Cys Gly Arg Ser Gly Glu Asn Phe Asp Lys Phe Phe Thr
1               5                  10                  15

Arg Ala Ala Pro Ala Leu Thr Pro Pro Asp Arg Leu Val Leu Ala Ser
            20                  25                  30

Ile Asp Gln Ala Asp Phe Gln Gly Phe Thr Tyr Val Asn Pro Asp Phe
        35                  40                  45

Val His Pro Asp Ala Arg Ser Pro Thr Ser Pro Val Pro Val Pro Val
    50                  55                  60

Met
65

<210> SEQ ID NO 23
<211> LENGTH: 6
<212> TYPE: PRT
<213> ORGANISM: Artificial
<220> FEATURE:
<223> OTHER INFORMATION: fragment derived from SEQ ID NO:22

<400> SEQUENCE: 23

Gly Arg Ser Gly Glu Asn
1               5

<210> SEQ ID NO 24
<211> LENGTH: 8
<212> TYPE: PRT
<213> ORGANISM: Artificial
<220> FEATURE:
<223> OTHER INFORMATION: fragment derived from SEQ ID NO:22

<400> SEQUENCE: 24

Pro Cys Gly Arg Ser Gly Glu Asn
1               5

<210> SEQ ID NO 25
<211> LENGTH: 6
<212> TYPE: PRT
<213> ORGANISM: Artificial
<220> FEATURE:
<223> OTHER INFORMATION: modified fragment derived from SEQ ID NO:22

<400> SEQUENCE: 25

Gly Lys Ser Gly Glu Asn
1               5

<210> SEQ ID NO 26
<211> LENGTH: 55
<212> TYPE: PRT
<213> ORGANISM: Artificial
<220> FEATURE:
<223> OTHER INFORMATION: V5 domain of the human deltaPKC isozyme

<400> SEQUENCE: 26

Pro Lys Val Lys Ser Pro Arg Asp Tyr Ser Asn Phe Asp Gln Glu Phe
1               5                  10                  15

Leu Asn Glu Lys Ala Arg Leu Ser Tyr Ser Asp Lys Asn Leu Ile Asp
            20                  25                  30

Ser Met Asp Gln Ser Ala Phe Ala Gly Phe Ser Phe Val Asn Pro Lys
        35                  40                  45

Phe Glu His Leu Leu Glu Asp
    50                  55
```

<210> SEQ ID NO 27
<211> LENGTH: 8
<212> TYPE: PRT
<213> ORGANISM: Artificial
<220> FEATURE:
<223> OTHER INFORMATION: fragment derived from SEQ ID NO:26

<400> SEQUENCE: 27

Val Lys Ser Pro Arg Asp Tyr Ser
1               5

<210> SEQ ID NO 28
<211> LENGTH: 11
<212> TYPE: PRT
<213> ORGANISM: Artificial
<220> FEATURE:
<223> OTHER INFORMATION: fragment derived from SEQ ID NO:26

<400> SEQUENCE: 28

Pro Lys Val Lys Ser Pro Arg Asp Tyr Ser Asn
1               5                   10

<210> SEQ ID NO 29
<211> LENGTH: 9
<212> TYPE: PRT
<213> ORGANISM: Artificial
<220> FEATURE:
<223> OTHER INFORMATION: modified fragment derived from SEQ ID NO:26

<400> SEQUENCE: 29

Val Lys Ser Pro Cys Arg Asp Tyr Ser
1               5

<210> SEQ ID NO 30
<211> LENGTH: 8
<212> TYPE: PRT
<213> ORGANISM: Artificial
<220> FEATURE:
<223> OTHER INFORMATION: modified fragment derived from SEQ ID NO:26

<400> SEQUENCE: 30

Ile Lys Ser Pro Arg Leu Tyr Ser
1               5

<210> SEQ ID NO 31
<211> LENGTH: 6
<212> TYPE: PRT
<213> ORGANISM: Artificial
<220> FEATURE:
<223> OTHER INFORMATION: fragment derived from SEQ ID NO:26

<400> SEQUENCE: 31

Lys Asn Leu Ile Asp Ser
1               5

<210> SEQ ID NO 32
<211> LENGTH: 51
<212> TYPE: PRT
<213> ORGANISM: Artificial
<220> FEATURE:
<223> OTHER INFORMATION: V5 domain of the human epsilonPKC isozyme

<400> SEQUENCE: 32

Pro Arg Ile Lys Thr Lys Arg Asp Val Asn Asn Phe Asp Gln Asp Phe
1               5                   10                  15

Thr Arg Glu Glu Pro Val Leu Thr Leu Val Asp Glu Ala Ile Val Lys
            20                  25                  30

```
Gln Ile Asn Gln Glu Glu Phe Lys Gly Phe Ser Tyr Phe Gly Glu Asp
        35                  40                  45
Leu Met Pro
    50

<210> SEQ ID NO 33
<211> LENGTH: 7
<212> TYPE: PRT
<213> ORGANISM: Artificial
<220> FEATURE:
<223> OTHER INFORMATION: fragment derived from SEQ ID NO:32

<400> SEQUENCE: 33

Ile Lys Thr Lys Arg Asp Val
1               5

<210> SEQ ID NO 34
<211> LENGTH: 10
<212> TYPE: PRT
<213> ORGANISM: Artificial
<220> FEATURE:
<223> OTHER INFORMATION: fragment derived from SEQ ID NO:32

<400> SEQUENCE: 34

Thr Lys Arg Asp Val Asn Asn Phe Asp Gln
1               5                   10

<210> SEQ ID NO 35
<211> LENGTH: 7
<212> TYPE: PRT
<213> ORGANISM: Artificial
<220> FEATURE:
<223> OTHER INFORMATION: modified fragment derived from SEQ ID NO:32

<400> SEQUENCE: 35

Cys Glu Ala Ile Val Lys Gln
1               5

<210> SEQ ID NO 36
<211> LENGTH: 7
<212> TYPE: PRT
<213> ORGANISM: Artificial
<220> FEATURE:
<223> OTHER INFORMATION: modified fragment derived from SEQ ID NO:32

<400> SEQUENCE: 36

Ile Lys Thr Lys Arg Leu Ile
1               5

<210> SEQ ID NO 37
<211> LENGTH: 6
<212> TYPE: PRT
<213> ORGANISM: Artificial
<220> FEATURE:
<223> OTHER INFORMATION: fragment derived from SEQ ID NO:32

<400> SEQUENCE: 37

Glu Ala Ile Val Lys Gln
1               5

<210> SEQ ID NO 38
<211> LENGTH: 51
<212> TYPE: PRT
<213> ORGANISM: Artificial
<220> FEATURE:
<223> OTHER INFORMATION: V5 domain of the human etaPKC isozyme
```

```
<400> SEQUENCE: 38

Pro Arg Ile Lys Ser Arg Glu Asp Val Ser Asn Phe Asp Pro Asp Phe
1               5                   10                  15

Ile Lys Glu Glu Pro Val Leu Thr Pro Ile Asp Glu Gly His Leu Pro
            20                  25                  30

Met Ile Asn Gln Asp Glu Phe Arg Asn Phe Ser Tyr Val Ser Pro Glu
        35                  40                  45

Leu Gln Pro
    50

<210> SEQ ID NO 39
<211> LENGTH: 8
<212> TYPE: PRT
<213> ORGANISM: Artificial
<220> FEATURE:
<223> OTHER INFORMATION: fragment derived from SEQ ID NO:38

<400> SEQUENCE: 39

Ile Lys Ser Arg Glu Asp Val Ser
1               5

<210> SEQ ID NO 40
<211> LENGTH: 9
<212> TYPE: PRT
<213> ORGANISM: Artificial
<220> FEATURE:
<223> OTHER INFORMATION: fragment derived from SEQ ID NO:38

<400> SEQUENCE: 40

Pro Arg Ile Lys Ser Arg Glu Asp Val
1               5

<210> SEQ ID NO 41
<211> LENGTH: 8
<212> TYPE: PRT
<213> ORGANISM: Artificial
<220> FEATURE:
<223> OTHER INFORMATION: modified fragment derived from SEQ ID NO:38

<400> SEQUENCE: 41

Val Arg Ser Arg Glu Asp Val Ser
1               5

<210> SEQ ID NO 42
<211> LENGTH: 6
<212> TYPE: PRT
<213> ORGANISM: Artificial
<220> FEATURE:
<223> OTHER INFORMATION: modified fragment derived from SEQ ID NO:38

<400> SEQUENCE: 42

Glu Gly His Asp Pro Met
1               5

<210> SEQ ID NO 43
<211> LENGTH: 6
<212> TYPE: PRT
<213> ORGANISM: Artificial
<220> FEATURE:
<223> OTHER INFORMATION: fragment derived from SEQ ID NO:38

<400> SEQUENCE: 43

Glu Gly His Leu Pro Met
1               5
```

<210> SEQ ID NO 44
<211> LENGTH: 56
<212> TYPE: PRT
<213> ORGANISM: Artificial
<220> FEATURE:
<223> OTHER INFORMATION: V5 domain of the human iotaPKC isozyme

<400> SEQUENCE: 44

Pro Asn Ile Ser Gly Glu Phe Gly Leu Asp Asn Phe Asp Ser Gln Phe
1               5                   10                  15

Thr Asn Glu Pro Val Gln Leu Thr Pro Asp Asp Asp Ile Val Arg
            20                  25                  30

Lys Ile Asp Gln Ser Glu Phe Glu Gly Phe Glu Tyr Ile Asn Pro Leu
        35                  40                  45

Leu Met Ser Ala Glu Glu Cys Val
    50                  55

<210> SEQ ID NO 45
<211> LENGTH: 8
<212> TYPE: PRT
<213> ORGANISM: Artificial
<220> FEATURE:
<223> OTHER INFORMATION: fragment derived from SEQ ID NO:44

<400> SEQUENCE: 45

Ile Ser Gly Glu Phe Gly Leu Asp
1               5

<210> SEQ ID NO 46
<211> LENGTH: 7
<212> TYPE: PRT
<213> ORGANISM: Artificial
<220> FEATURE:
<223> OTHER INFORMATION: fragment derived from SEQ ID NO:44

<400> SEQUENCE: 46

Asp Asp Asp Ile Val Arg Lys
1               5

<210> SEQ ID NO 47
<211> LENGTH: 8
<212> TYPE: PRT
<213> ORGANISM: Artificial
<220> FEATURE:
<223> OTHER INFORMATION: modified fragment derived from SEQ ID NO:44

<400> SEQUENCE: 47

Cys Ser Gly Glu Phe Gly Leu Asp
1               5

<210> SEQ ID NO 48
<211> LENGTH: 6
<212> TYPE: PRT
<213> ORGANISM: Artificial
<220> FEATURE:
<223> OTHER INFORMATION: fragment derived from SEQ ID NO:44

<400> SEQUENCE: 48

Asp Asp Ile Val Arg Lys
1               5

<210> SEQ ID NO 49
<211> LENGTH: 192
<212> TYPE: PRT
<213> ORGANISM: Artificial

```
<220> FEATURE:
<223> OTHER INFORMATION: V5 domain of the human muPKC isozyme

<400> SEQUENCE: 49

Pro Gln Val Lys Leu Cys Asp Phe Gly Phe Ala Arg Ile Ile Gly Glu
1               5                   10                  15

Lys Ser Phe Arg Arg Ser Val Val Gly Thr Pro Ala Tyr Leu Ala Pro
                20                  25                  30

Glu Val Leu Arg Asn Lys Gly Tyr Asn Arg Ser Leu Asp Met Trp Ser
            35                  40                  45

Val Gly Val Ile Ile Tyr Val Ser Leu Ser Gly Thr Phe Pro Phe Asn
        50                  55                  60

Glu Asp Glu Asp Ile His Asp Gln Ile Gln Asn Ala Ala Phe Met Tyr
65                  70                  75                  80

Pro Pro Asn Pro Trp Lys Glu Ile Ser His Glu Ala Ile Asp Leu Ile
                85                  90                  95

Asn Asn Leu Leu Gln Val Lys Met Arg Lys Arg Tyr Ser Val Asp Lys
            100                 105                 110

Thr Leu Ser His Pro Trp Leu Gln Asp Tyr Gln Thr Trp Leu Asp Leu
        115                 120                 125

Arg Glu Leu Glu Cys Lys Ile Gly Glu Arg Tyr Ile Thr His Glu Ser
    130                 135                 140

Asp Asp Leu Arg Trp Glu Lys Tyr Ala Gly Glu Gln Arg Leu Gln Tyr
145                 150                 155                 160

Pro Thr His Leu Ile Asn Pro Ser Ala Ser His Ser Asp Thr Pro Glu
                165                 170                 175

Thr Glu Glu Thr Glu Met Lys Ala Leu Gly Glu Arg Val Ser Ile Leu
            180                 185                 190

<210> SEQ ID NO 50
<211> LENGTH: 8
<212> TYPE: PRT
<213> ORGANISM: Artificial
<220> FEATURE:
<223> OTHER INFORMATION: fragment derived from SEQ ID NO:49

<400> SEQUENCE: 50

Val Lys Leu Cys Asp Phe Gly Phe
1               5

<210> SEQ ID NO 51
<211> LENGTH: 10
<212> TYPE: PRT
<213> ORGANISM: Artificial
<220> FEATURE:
<223> OTHER INFORMATION: fragment derived from SEQ ID NO:49

<400> SEQUENCE: 51

Gln Val Lys Leu Cys Asp Phe Gly Phe Ala
1               5                   10

<210> SEQ ID NO 52
<211> LENGTH: 8
<212> TYPE: PRT
<213> ORGANISM: Artificial
<220> FEATURE:
<223> OTHER INFORMATION: modified fragment derived from SEQ ID NO:49

<400> SEQUENCE: 52

Ile Arg Leu Cys Asp Phe Ala Phe
1               5
```

-continued

```
<210> SEQ ID NO 53
<211> LENGTH: 54
<212> TYPE: PRT
<213> ORGANISM: Artificial
<220> FEATURE:
<223> OTHER INFORMATION: V5 domain of the human thetaPKC isozyme

<400> SEQUENCE: 53

Pro Lys Val Lys Ser Pro Phe Asp Cys Ser Asn Phe Asp Lys Glu Phe
1               5                   10                  15

Leu Asn Glu Lys Pro Arg Leu Ser Phe Ala Asp Arg Ala Leu Ile Asn
            20                  25                  30

Ser Met Asp Gln Asn Met Phe Arg Asn Phe Ser Phe Met Asn Pro Gly
        35                  40                  45

Met Glu Arg Leu Ile Ser
    50

<210> SEQ ID NO 54
<211> LENGTH: 8
<212> TYPE: PRT
<213> ORGANISM: Artificial
<220> FEATURE:
<223> OTHER INFORMATION: fragment derived from SEQ ID NO:53

<400> SEQUENCE: 54

Val Lys Ser Pro Phe Asp Cys Ser
1               5

<210> SEQ ID NO 55
<211> LENGTH: 7
<212> TYPE: PRT
<213> ORGANISM: Artificial
<220> FEATURE:
<223> OTHER INFORMATION: fragment derived from SEQ ID NO:53

<400> SEQUENCE: 55

Asp Arg Ala Leu Ile Asn Ser
1               5

<210> SEQ ID NO 56
<211> LENGTH: 8
<212> TYPE: PRT
<213> ORGANISM: Artificial
<220> FEATURE:
<223> OTHER INFORMATION: modified fragment derived from SEQ ID NO:53

<400> SEQUENCE: 56

Val Arg Ser Pro Phe Asp Cys Ser
1               5

<210> SEQ ID NO 57
<211> LENGTH: 6
<212> TYPE: PRT
<213> ORGANISM: Artificial
<220> FEATURE:
<223> OTHER INFORMATION: fragment derived from SEQ ID NO:53

<400> SEQUENCE: 57

Arg Ala Leu Ile Asn Ser
1               5

<210> SEQ ID NO 58
<211> LENGTH: 56
<212> TYPE: PRT
<213> ORGANISM: Artificial
```

```
<220> FEATURE:
<223> OTHER INFORMATION: V5 domain of the human xiPKC isozyme

<400> SEQUENCE: 58

Pro Gln Ile Thr Asp Asp Tyr Gly Leu Asp Asn Phe Asp Thr Gln Phe
1               5                   10                  15

Thr Ser Glu Pro Val Gln Leu Thr Pro Asp Asp Glu Asp Ala Ile Lys
            20                  25                  30

Arg Ile Asp Gln Ser Glu Phe Glu Gly Phe Glu Tyr Ile Asn Pro Leu
        35                  40                  45

Leu Leu Ser Thr Glu Glu Ser Val
    50                  55

<210> SEQ ID NO 59
<211> LENGTH: 8
<212> TYPE: PRT
<213> ORGANISM: Artificial
<220> FEATURE:
<223> OTHER INFORMATION: fragment derived from SEQ ID NO:58

<400> SEQUENCE: 59

Ile Thr Asp Asp Tyr Gly Leu Asp
1               5

<210> SEQ ID NO 60
<211> LENGTH: 7
<212> TYPE: PRT
<213> ORGANISM: Artificial
<220> FEATURE:
<223> OTHER INFORMATION: fragment derived from SEQ ID NO:58

<400> SEQUENCE: 60

Asp Asp Tyr Gly Leu Asp Asn
1               5

<210> SEQ ID NO 61
<211> LENGTH: 8
<212> TYPE: PRT
<213> ORGANISM: Artificial
<220> FEATURE:
<223> OTHER INFORMATION: modified fragment derived from SEQ ID NO:58

<400> SEQUENCE: 61

Ile Thr Asp Asp Tyr Gly Asp Leu
1               5

<210> SEQ ID NO 62
<211> LENGTH: 5
<212> TYPE: PRT
<213> ORGANISM: Artificial
<220> FEATURE:
<223> OTHER INFORMATION: modified fragment derived from SEQ ID NO:58

<400> SEQUENCE: 62

Glu Asp Ala Ile Arg
1               5

<210> SEQ ID NO 63
<211> LENGTH: 6
<212> TYPE: PRT
<213> ORGANISM: Artificial
<220> FEATURE:
<223> OTHER INFORMATION: fragment derived from SEQ ID NO:58
```

```
-continued

<400> SEQUENCE: 63

Glu Asp Ala Ile Lys Arg
1               5

<210> SEQ ID NO 64
<211> LENGTH: 6
<212> TYPE: PRT
<213> ORGANISM: Artificial
<220> FEATURE:
<223> OTHER INFORMATION: fragment derived from the V5 domain of the
      human muPKC isozyme

<400> SEQUENCE: 64

Ser Asp Ser Pro Glu Ala
1               5

<210> SEQ ID NO 65
<211> LENGTH: 10
<212> TYPE: PRT
<213> ORGANISM: Artificial
<220> FEATURE:
<223> OTHER INFORMATION: Tat-derived carrier peptide (Tat 47-57)

<400> SEQUENCE: 65

Tyr Gly Lys Lys Arg Arg Gln Arg Arg Arg
1               5                   10

<210> SEQ ID NO 66
<211> LENGTH: 17
<212> TYPE: PRT
<213> ORGANISM: Artificial
<220> FEATURE:
<223> OTHER INFORMATION: Drosophila Antennapedia homeodomain-derived
      carrier peptide

<400> SEQUENCE: 66

Cys Arg Gln Ile Lys Ile Trp Phe Gln Asn Arg Arg Met Lys Trp Lys
1               5                   10                  15

Lys
```